(12) United States Patent
Lauer

(10) Patent No.: US 9,248,224 B2
(45) Date of Patent: Feb. 2, 2016

(54) CONNECTION DEVICE FOR CONNECTING AT LEAST ONE EXTERNAL FUNCTIONAL DEVICE TO AN ARRANGEMENT, AND AN ARRANGEMENT INCLUDING SUCH A CONNECTION DEVICE

(75) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 751 days.

(21) Appl. No.: 13/388,515

(22) PCT Filed: Jul. 29, 2010

(86) PCT No.: PCT/EP2010/004642
§ 371 (c)(1),
(2), (4) Date: Feb. 23, 2012

(87) PCT Pub. No.: WO2011/015309
PCT Pub. Date: Feb. 10, 2011

(65) Prior Publication Data
US 2012/0141197 A1    Jun. 7, 2012

(30) Foreign Application Priority Data
Aug. 4, 2009  (DE) .................. 10 2009 036 101

(51) Int. Cl.
*A61M 1/14*    (2006.01)
*A61M 1/36*    (2006.01)

(52) U.S. Cl.
CPC .............. *A61M 1/14* (2013.01); *A61M 1/3621* (2013.01); *A61M 2205/12* (2013.01); *A61M 2209/08* (2013.01); *Y10T 403/7015* (2015.01)

(58) Field of Classification Search
CPC ................... A61M 2205/12; A61M 2205/121; A61M 39/227; A61M 2209/08
USPC ............ 403/31, 34–39, 325, 327, 321, 322.1; 604/152, 153
See application file for complete search history.

(56) References Cited

U.S. PATENT DOCUMENTS

| | | | |
|---|---|---|---|
| 5,192,058 A * | 3/1993 | VanDalsem et al. ............ 269/24 |
| 5,614,677 A | 3/1997 | Wamsiedler et al. |
| 8,267,612 B2 * | 9/2012 | Yeh ............................ 403/322.2 |
| 8,328,454 B2 * | 12/2012 | McAndrews et al. ...... 403/109.7 |
| 2005/0020959 A1 | 1/2005 | Brugger et al. |

FOREIGN PATENT DOCUMENTS

| | | |
|---|---|---|
| DE | 44 19 593 A1 | 12/1995 |
| EP | 0685721 A1 | 12/1995 |
| JP | 07-333093 | 12/1995 |

OTHER PUBLICATIONS

International Search Report from PCT/EP2010/004642, mailed on Jan. 12, 2010.

* cited by examiner

*Primary Examiner* — Daniel Wiley
(74) *Attorney, Agent, or Firm* — Kenyon & Kenyon LLP

(57) ABSTRACT

A connection device, and an arrangement comprising such a connection device, for connecting, in particular coupling, at least one external functional device to an arrangement by pressing the external functional device. The connection device comprises at least one reception device having at least one first contact portion. It further comprises at least one pressing device which is configured for transferring at least the first contact portion from a first position into the second position by applying a first force ($F_1$) and a second force ($F_2$). The two forces ($F_1$) and ($F_2$) are of a different magnitude.

13 Claims, 6 Drawing Sheets

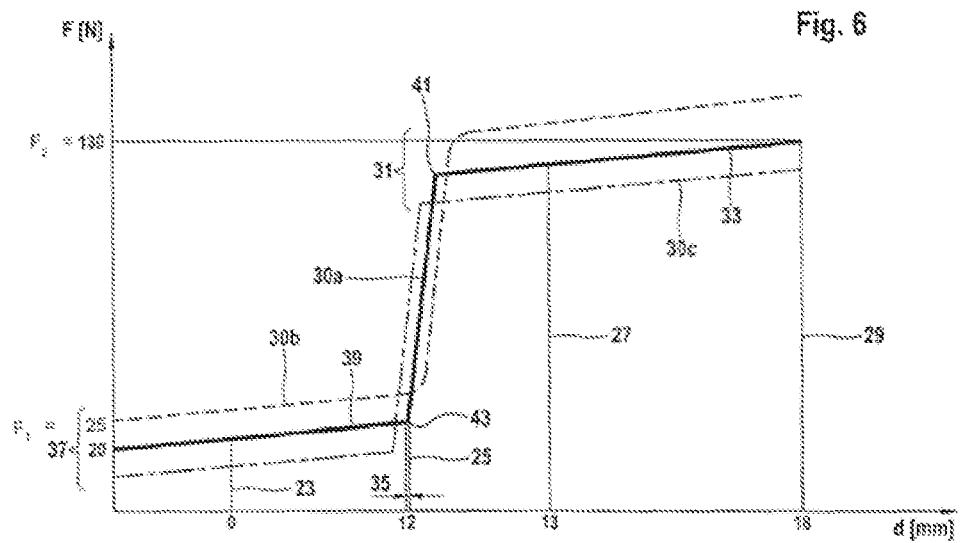

CONNECTION DEVICE FOR CONNECTING AT LEAST ONE EXTERNAL FUNCTIONAL DEVICE TO AN ARRANGEMENT, AND AN ARRANGEMENT INCLUDING SUCH A CONNECTION DEVICE

CROSS REFERENCE TO RELATED APPLICATIONS

This is a 371 national phase application of PCT/EP2010/004642 filed Jul. 29, 2010, claiming priority to German Patent Application No. 10 2009 036 101.4 filed Aug. 4, 2009.

FIELD OF INVENTION

The present invention relates to a connection device for connecting at least one external functional device to an arrangement by pressing the external functional device. It further relates to a method for connecting. The present invention moreover relates to an arrangement which includes a connection device in accordance with the invention.

BACKGROUND OF THE INVENTION

In arrangements such as, for example, medical-technical treatment apparatuses, laboratory-technical arrangements or also arrangements for the food production, it is frequently necessary to connect, in particular couple, external functional device such as tubes, heat exchangers, measurement chambers or multi-functional disposable cassettes to the arrangement prior to its use.

Connecting or coupling such an external functional device to the arrangement takes place with the aid of a connection device comprising a reception device for receiving the external functional device and a pressing device for exerting pressure on the external functional device.

SUMMARY OF THE INVENTION

It is an object of the present invention to provide a further connection device for connecting at least one functional device to an arrangement. It furthermore is an aim of the present invention to specify a method for connecting at least one external functional device by using such a connection device, as well as an arrangement comprising such a connection device.

The connection device of the invention comprises at least one reception device having at least one first contact portion for receiving at least one external functional device between the first contact portion and one or several further contact portions. It further comprises at least one pressing device for pressing the at least one external functional device between the first contact portion and the further contact portion. The pressing device is configured for transferring at least the first contact portion from a first position, in particular a set-up position, into a second position by applying a first force $F_1$ and a second force $F_2$ of a different magnitude.

An "external functional device" as used in the present may be a tube, a heat exchanger, a measurement device, a multi-functional disposable cassette, any single-use article, or the like. It is noted in the context of the present disclosure that the expression "may comprise" or "may be" is synonymous with the expression "preferably comprises" or "preferably is" as also used in the present and elsewhere.

The external functional device may transmit energy, measurement values and/or mechanical movements and forces to the arrangement or receive these from the latter. It may, however, also merely be held by the arrangement while not interacting or being in signal communication with it.

An "arrangement" in the sense of the present invention may be a medical-technical arrangement such as, for example, a blood treatment apparatus, e.g. a dialysis apparatus, an arrangement in laboratory technology, an arrangement in drug or food production, etc.

In accordance with the invention, the expression "pressing" as presently used may designate retaining by means of pressure, in particular by means of pressing, pinching, or the like.

The connection device of the invention may be intended for coupling one or several external functional device.

Such pressing may preferably be of a temporary nature. The external functional device coupled by pressing may be fastened in a releasable manner. It may be fastened so as to be exchangeable.

In addition to the reception device, further devices for pressing or retaining the external functional device such as, for example, loops, lugs, straps, spring-loaded latches, levers and the like may be provided.

The expression "connecting" and/or "coupling" as presently used may designate or encompass a functional and/or mechanical connection of the external functional device to a coupling partner on the side of the arrangement.

A "coupling partner of the arrangement" may, e.g., be a measurement device such as, for example, a sensor.

A "reception device" in the sense of the present invention is a device that is suited for receiving at least one external functional device.

The dimension of an opening or of a gap of the reception device for receiving the one or several external functional device may be configured in correspondence to the height, length, width, diameter etc. of the one or several external functional device for specifically receiving it/them.

The dimension may be made to be variable.

The reception device comprises at least one first contact portion.

The "first contact portion" may be a presser plate. It may have a flat or curved configuration. It may enter into dot-shaped or planar contact with the external functional device. It may comprise a portion corresponding in its geometry to an extension of the external functional device to be coupled in the pressed or non-pressed condition.

The first contact portion may serve in a multi-functional manner for coarse alignment, for locking, and/or for transmitting a pressing force to the external functional device.

The first contact portion may in a given case comprise further devices for supporting pressing the external functional device and/or retaining the latter.

The "further contact portion" is preferably provided on the very connection device of the invention or on an arrangement.

The further contact portion may have the same configuration as the first contact portion. It may be a coupling surface. The expression "coupling surface" may designate, for example, at least one portion of an upper side of a carrier member and/or of a support member and/or of a measurement device or the like of the arrangement or of the connection device.

The first contact portion is configured to be movable. The further contact portion may be configured to be movable. At least one of the contact portions may be arranged to be rigid or in a rigid manner.

The first contact portion is arranged at a variable spacing d from the further contact portion. The spacing d may in particular be varied by moving the first contact portion in a direction towards the further contact portion.

Jointly or together with at least one further portion of the connection device of the invention or of an arrangement such as, for example, a carrier member, the contact portions may form a C-shaped portion.

The reception device may comprise at least one installation gap that is variable in its height or width, and into which the external functional device may be inserted in the set-up position and from which the external functional device may again be removed according to need.

A "pressing device" in the sense of the present invention is adapted for pressing the external functional device by transferring at least the first contact portion and/or the further contact portion from a first position of the connection device into a second position in which pressure is exerted on the external functional device by means of the contact portions.

Such "pressing" may be achieved by applying respective first and second mechanical, hydraulic, pneumatic, electromagnetic, inductive or some other suitable forces $F_1$ and $F_2$, or combinations thereof, to at least the first contact portion.

In this regard, the first force $F_1$ may, for example, be generated mechanically, however the second force $F_2$ may, for example, be generated pneumatically, or vice versa.

The first position may be a set-up position.

A "set-up position" in the sense of the present invention is a position in which the first contact portion is spaced apart from the further contact portion by a spacing $d_1$.

In the set-up position, the opening of the reception device is sufficiently large for admitting insertion of at least one external functional device.

Furthermore, the opening may also be large enough for introducing body parts, in particular fingers into it.

In accordance with the invention, the "second position" is a position in which the first contact portion is spaced apart from the further contact portion by a spacing $d_2$, with the second spacing $d_2$ being smaller than the first spacing $d_1$.

In the second position, the opening of the connection device may be too small for inserting the external functional device and/or for introducing body parts.

Due to the application of two different forces $F_1$ and $F_2$ during operation of the pressing device, it is advantageously possible to obtain a stepped force effect.

Such a stepped force effect may allow one to intentionally influence parameters of the movement such as, for example, the velocity, the duration of the movement, the acceleration, the force distribution, positions, and the like. It may furthermore admit a variable layout of the constructional space of the connection device, of the arrangement, of single components thereof and/or of further devices and elements.

In a preferred embodiment of the present invention, the pressing device is configured for transferring at least the first contact portion from the first position into the second position by the first force $F_1$ and/or the second force $F_2$ depending on the spacing d.

The force required for transferring the at least one movable contact portion between the first and second positions may be given a magnitude in dependence on the actual, existing spacing d between the first contact portion and the further contact portion, or may be variable.

The transition from the first position into the second position may take place in an intentional manner, i.e., in a manner fixed or predetermined in advance. In particular, it is possible to provide abrupt changes in the force evolution.

In a further preferred embodiment of the present invention, the pressing device comprises at least two energy storage and/or force transmitting devices for transferring at least the first contact portion from the first position into the second position.

The energy storage and/or force transmitting device may be suited for receiving and storing energy and/or transmitting force, such as, for example, pneumatic force.

As is provided in a further preferred embodiment, the pressing device may comprise only a single energy storage and/or force transmitting device having, e.g., the form of a spring, wherein the latter comprises or generates a non-continuous or "broken" path-dependent force evolution in a force/path diagram upon transition from one position into another one. Stops and coupling links which in a given case are necessary for this purpose may be further encompassed by the pressing device.

In a further preferred embodiment of the present invention, the first energy storage and/or force transmitting device is configured to apply and/or transmit a first force $F_1$, and a second energy storage and/or force transmitting device is configured to apply and/or transmit a second force $F_2$. The first force $F_1$ may be lower or weaker than the second force $F_2$. The first force $F_1$ and the second force $F_2$ might have a same amount or magnitude. The first force $F_1$ might also be higher or stronger than the second force $F_2$.

The first force $F_1$ and/or the second force $F_2$ may each designate a force range or range of forces or make up such a range of forces. They may, however, in turn also designate a discrete force level or an absolute force. The first force $F_1$ and the second force $F_2$ may also overlap each other, i.e., their force ranges may merge with each other.

Examples for force ranges of the forces $F_1$ and $F_2$ are shown in FIG. 6. Thus, e.g., $F_1$ may represent or designate a force range of lower forces, and $F_2$ may represent or designate a force range of higher forces.

In an even further preferred embodiment of the present invention, the first and the second energy storage and/or force transmitting devices are arranged such that the first energy storage and/or force transmitting device applies and/or transmits the first force $F_1$ during the transition from the first position to a position presently designated as a force change position, and that the second energy storage and/or force transmitting device applies and/or transmits the second force $F_2$ during the transition from the force change position to the second position.

During the transition from the first position into the second position, the first force $F_1$ is initially applied. Having reached the force change position, the second force $F_2$ is applied. The first force $F_1$ may be a sum of forces, for example of spring forces $FE_1$ of a first spring and $FE_2$ of a second spring while disregarding frictional and other forces. The second force $F_2$ may correspond exactly or approximately to the force $FE_2$ of the second spring.

As overlaps are possible, the force change position should not exclusively be understood to be a defined point at which the change of force takes place. The force change position may rather designate a transitional range involving a substantial alteration of the force acting on the contact portions.

The first force $F_1$ may be lower or weaker than the second force $F_2$ as is shown, for example, in the force/path diagram of FIG. 6.

The first force $F_1$ may bring about a higher displacement velocity v of the moved contact portion than the second force $F_2$. The velocity at which the connection device of the invention is displaced upon transition from the first position into the second position may pass from a higher velocity to a lower velocity at the force change position.

In a further preferred embodiment of the present invention, the energy storage and/or force transmitting devices are configured as stress-strain elements. Such stress-strain elements are preferably realized as a first and a second spring.

The first and the second spring may be arranged in a releasable or non-releasable manner in combination with spring dowels—as is exemplarily explained in the appended drawings and in the description thereof—and/or movement stops.

The first and the second spring may be arranged in parallel and/or nested, preferably in a coaxial manner. They may be arranged in series, arranged in parallel in side-by-side relationship, or arranged coaxially in a back-to-front relationship.

The first and the second spring may be helical springs, wound torsion springs, leg springs, torsion and/or torque rods, spiral springs, flat coil springs, leaf springs, disk springs, diaphragm springs, pneumatic springs, gas pressure springs, elastomer springs, annular springs, or the like.

The springs may be made of, or comprise, spring steels such as, e.g., 38Si7, 61SiCr7, 52CrMoV4, 51CrV4 (according to standard EN 10089), spring steel 1.4310, of copper-beryllium alloys, rubber, compound fiber materials such as fiberglass-reinforced plastics of polyester resin, epoxy resin or polyamide, nickel alloys and/or the like.

In a preferred embodiment of the present invention, the at least one external functional device is adapted to be coupled by frictional and/or form closure connection to the arrangement, for functionally coupling the external functional device to a coupling partner on the side of the arrangement.

Such "functional coupling" of the external functional device to a coupling partner on the side of the arrangement device that the at least one external functional device and the at least one coupling partner on the side of the arrangement are connected to each other for achieving a function such as, for example, for the transmission of measurement values.

Such coupling may take place by direct connection of the at least one external functional device to the coupling partner and/or by connection through the intermediary of an electrical line, a cable for data transmission and/or wireless connection such as, for example, infrared, Bluetooth, WLAN, RFID (Radio Frequency Identification; identification with the aid of electromagnetic waves) and the like. Further devices for coupling or functional connection may be provided.

Coupling may moreover take place by form closure or frictional connection, by magnetic or electromagnetic attraction or repulsion, negative pressure or vacuum suction, etc. Corresponding devices may be provided.

In a further preferred embodiment of the present invention, the connection device of the invention may comprise at least one carrier member and/or support member adapted to be fixedly integrated on the arrangement.

A "carrier member" may be a coupling partner and/or an outer carrier and/or an inner carrier of the arrangement.

A "support member" may be a connection carrier, a lower dowel stop as is exemplarily explained in the appended drawings and the description thereof, an opening stop, an upper dowel stop, and/or a coupling stop.

Such a support member may be suited for limiting a movement of the movable device of the device of the invention.

Fixedly integrated devices are advantageously liable to less wear. They may serve as a housing, as a protection of the connection device of the invention, for receiving the coupling partner, and the like. The support members may furthermore prevent the movable device from slipping out.

In a preferred embodiment of the present invention, at least one further contact portion, for example an outer carrier and/or a coupling partner, is adapted to be fixedly integrated on the arrangement.

In a further preferred embodiment of the present invention, the second position is a work position.

In the "work position" in the sense of the present invention, the at least one external functional device is pressed with the arrangement for its intended use.

In the work position, in particular the actual useful coupling between the external functional device and the coupling partner may take place. The external functional device may be coupled to the arrangement-side coupling partner free from mechanical play and subjected to a force. The external functional device is functionally connected to the coupling partner.

In a further preferred embodiment of the present invention, the second position is a closure position. In the latter, the first contact portion may rest on the further contact portion or on a portion of the arrangement, e.g. a housing portion, or represent a seal with the latter.

In the closure position, the first contact portion may preferably rest on the further contact portion in a gas- and/or liquid-tight manner, in a generally particularly preferred manner in a fluid-tight manner.

The first contact portion may be a lid. Resting of the first contact portion on the further contact portion or the creation of a seal with the latter may advantageously protect the device of the invention against penetration of dirt and/or other foreign matter into its interior or into an interior of the arrangement. Furthermore, it is preferably possible to wipe over such a seal or clean it in some other manner without humidity etc. entering into the interior of the arrangement. In accordance with the invention, further devices for sealing the device of the invention may be provided, such as, for example, sealing rings, spring-loaded latches, and the like.

In a further preferred embodiment of the present invention, the external functional device is a single-use product such as a tube, a conduit, an extracorporeal blood circuit of a dialysis apparatus, or the like.

In a further preferred embodiment, the external functional device comprises a pressure measurement disposable, in particular a pressure measurement disposable which is a component part of a disposable tube set, or is realized as such a pressure measurement disposable. The coupling partner comprises a pressure sensor on a blood treatment apparatus for an extracorporeal blood treatment, in particular a dialysis apparatus, or is such a pressure sensor. The pressure measurement disposable is adapted to be coupled to the pressure sensor for measuring a pressure inside the pressure measurement disposable.

In a further preferred embodiment, the connection device of the invention makes it also possible to initially operate with a lower, exemplary force $F_{11}<F_{22}$ upon transition from the first position into the second position, and only subsequently with the higher, exemplary force $F_{22}>F_{11}$. Here, it is possible to reduce a wide installation gap in which, e.g., a finger might be pinched, by using a force that is not injurious to the latter. In analogy, pressing by using the higher force is only performed from a width of the installation gap at which it is not possible any more to insert, e.g., a finger into the installation gap.

In a preferred manner, the velocity at which the gap is reduced starting out from the first position, e.g. the set-up position, may initially be set so low that sufficient time remains for pulling back a finger inadvertently introduced into the installation gap before the higher force for pressing begins to act.

As the method of the present invention relates to the use of a connection device of the present invention in accordance with the above description, reference is made to the explanations described in the foregoing in order to avoid repetitions. Respective advantages that are achievable with the connection device of the present invention may also be achieved in an undiminished manner with the method.

In a preferred embodiment of the method of the invention, which relates to the use of a connection device of the invention in accordance with the above description, in order to connect the external functional device at least a first contact portion is transferred from a first position into a second position by passing through a force change position, wherein a first force $F_1$ is applied and/or transmitted with the aid of a pressing device prior to reaching the force change position, and a second force $F_2$ after reaching or leaving it.

The second position may be a work position or a closure position.

In a further preferred embodiment of the method of the invention, in order to connect the external functional device, at least a first contact portion is transferred from the first position into the second position by passing through a force change position, wherein prior to reaching the force change position the transition takes place at a first displacement velocity $v_1$, and the transition from the force change position into the second position takes place at a second displacement velocity $v_2$. The first displacement velocity $v_1$ may be higher than the second displacement velocity $v_2$. It may be lower than the second displacement velocity $v_2$.

In a further preferred embodiment of the method of the invention, the second position is a work position.

The transition from the first position, in which a first pressure $p_1$ prevails in a work space, to the work position takes place in such a way that a second pressure $p_2$, which is lower than the first pressure $p_1$, is applied in the work space and the pressing device of the connection device of the invention is displaced into the work space until the external functional device is pressed with the arrangement in the work position. The force to be received by the external functional device may diminish from a higher second force $F_2$ to a lower first force $F_1$. Such a force evolution is exemplarily illustrated in FIG. 6, from right to left.

The "work space" should here be understood to be a space having a variable volume in which a pressure is built up and/or whereby a pressure may be exerted. Such a work space may be connected to a pressure port for applying and/or transmitting a pressure force.

In a further preferred embodiment of the method of the invention, the second position is a closure position.

The transition from the first position into the closure position may take place in such a way that a second pressure $p_2$ in the work space is lowered to zero or to a value close to zero. The energy storage and/or force transmitting device in the closure position may be subjected to only a low bias. The first contact portion rests on the further contact portion or on some other portion.

In the closure position, sealing of an interior of an arrangement against an outside may be obtained.

In a further preferred embodiment of the method of the invention, the external functional device comprises a pressure measurement disposable, in particular a pressure measurement disposable which is a component part of a disposable tube set, or is such a pressure measurement disposable. The coupling partner comprises a pressure sensor on a blood treatment apparatus for an extracorporeal blood treatment, in particular a dialysis apparatus, or is such a pressure sensor. The method includes coupling the pressure measurement disposable to the pressure sensor and measuring a pressure in the pressure measurement disposable by means of the pressure sensor. The process sequence of a pressure determination may be seen, for example, in DE 44 19 593 A1, the relevant contents of which are herewith fully incorporated by way of reference.

As the arrangement of the invention comprises a connection device of the invention for connecting at least one external functional device to an arrangement, reference is made to the explanations thereof described in the foregoing in order to avoid repetitions. Advantages that may be obtained with the connection device of the invention may also be obtained in an undiminished manner with the arrangement of the invention.

The arrangement of the invention may be any medical-technical arrangement, arrangement from laboratory technology or food production that is suited for the purposes of the present invention. In a preferred embodiment of the present invention, the arrangement of the invention is a blood treatment apparatus.

As is provided in a preferred embodiment, the arrangement of the invention may additionally comprise a control or regulation device which is suited and configured for controlling or regulating a pneumatically acting or pneumatically operable device of the connection device—e.g., an opening actor subassembly.

The control or regulation device may be a device for controlling or regulating as customarily provided on blood treatment arrangements or other arrangements. As an alternative, it may be provided separately from the latter.

The control or regulation device may be a CPU, comprise such a CPU, or be programmed in one.

Due to the fact that external functional devices are in practice generally retained or pressed by means of pressure, there is a risk that fingers of the person inserting the external functional device may be pinched between the contact portions. From the prior art various safety devices are known.

Thus it is known from DE 44 19 593 A1 to limit a force for pressing the external functional device to a value that is too low for fingers to get pinched. Other devices that are known from practice comprise a sensor which detects and reports the introduction of fingers etc.

In the present invention, a transition of the pressing device from a first position into a second one takes place, for example, with the aid of a first and a second spring having different spring forces $FE_1$ and $FE_2$, respectively, whereby a first force $F_1$ and a second force $F_2$ are obtainable. The spring forces $FE_1$ and $FE_2$ of the springs result from their spring characteristics; for instance, the linear spring characteristic—disregarding friction—is defined as: spring force=spring stiffness×spring excursion.

Depending on the mutual spacing of the contact portions, a stepped or abruptly changing application of force may be employed.

It is therefore possible to preferably and advantageously apply the full contact pressure only on a short displacement path at a widely opened installation gap corresponding, for example, to the thickness or to the diameter of the external functional device. Further closing of the connection device may advantageously take place at a reduced force, so that it is not possible to injure, e.g., fingers having gotten into the installation gap. This constitutes a possible advantage that may be achieved through the present invention.

With the present invention, it may furthermore advantageously be possible to increase a contact pressure of the connection device and thus obtain improved coupling. At the same time, it may advantageously be possible to reduce a risk of injury to the user in the above-described manner.

The present invention may thus advantageously allow an increase of the coupling force at no or only little additional expenditure of drive energy, for a part of the pressing path is performed under the low force of the displacement spring. This allows a comparatively simplified construction of the connection device of the invention in comparison with a prior-art connection device without differentiation between a first, low force and a second, higher force for displacing the contact portions.

As in most applications the rest periods of the arrangement in the closure position may be longer than the periods spent in the work position, the present invention advantageously allows a more gentle treatment of the structural components with regard to deformation, fatigue, wear and the like, as these will only be subjected to the lower force effect of the displacement spring while being in the closure position.

The force of the displacement spring may be selected to be so low that it still achieves the desired functions of resetting and sealing the machine arrangement. Thus, the potential pinching forces, displacement forces and load forces in the condition of rest may in many cases advantageously be selected to be lower than in a conventional arrangement having only one force stage which was chosen with a view to a pressing force that is just about admissible or required. This may advantageously result in a reduced demand of constructional space.

In the closure position of the present invention in which no external functional device is pressed or installed, it is furthermore advantageously possible to close the installation space, and in a given case also additional spaces, with the aid of the connection device of the invention. It may advantageously ensure a good cleaning comportment of the arrangement as well as a safe protection of an interior of the device of the invention and/or of the arrangement against the penetration of undesirable particles and liquids.

By means of the present invention, it is advantageously possible to constructively change installation spaces and forces. With the present invention, it may advantageously be possible to correspondingly adapt each functional portion and give it a design as optimal as possible.

The present invention is capable of advantageously satisfying the demands mentioned in the foregoing in a novel, safe, simple and cost-saving manner by a new arrangement of mechanical or other functional elements that are known per se.

As a stepped force effect as a function of the spacing of the contact portions may take place with the aid of the present invention, the utilization of other protection systems such as grids or sensors or controlled safety actors or complex obstacles to access may advantageously be omitted. This may advantageously reduce technical complexity at comparable or even improved safety.

In the event of a power and control failure, a safe process sequence may advantageously be effected with the present invention, particularly if mechanical energy storage and/or force transmitting devices are used. The possible pinching force or the width of the possible pinching or installation gaps, respectively, are always situated in the safe range as they are fixedly predetermined in a mechanical manner.

With the present invention the functional properties of the arrangement may advantageously be improved, for an increase of the pressing force in the work position to, for example, approximately three times the original value may be obtained. This may be obtained with the aid of the stepped force effect without having to carry out modifications on the basic dimensional ratios of the arrangement and of the external functional device and/or on the energetic layout of the arrangement, or having to accept hazards to the personnel.

The potential force to pinch body parts introduced into the installation gap of a set-up position, in particular fingers, may advantageously be reduced by the distribution of the applied force to different forces, e.g. a first and a second force.

The present invention may advantageously allow manual insertion of the external functional device by applying low skill and low force.

BRIEF DESCRIPTION OF THE DRAWINGS

In the following, the present invention shall be described by way of preferred exemplary embodiments while making reference to the appended schematic, highly simplified drawings. In the figures, same reference numerals are used for designating same elements, wherein:

FIG. 6 shows an example of a force/path diagram.

DETAILED DESCRIPTION OF THE DRAWINGS

Figure 1:
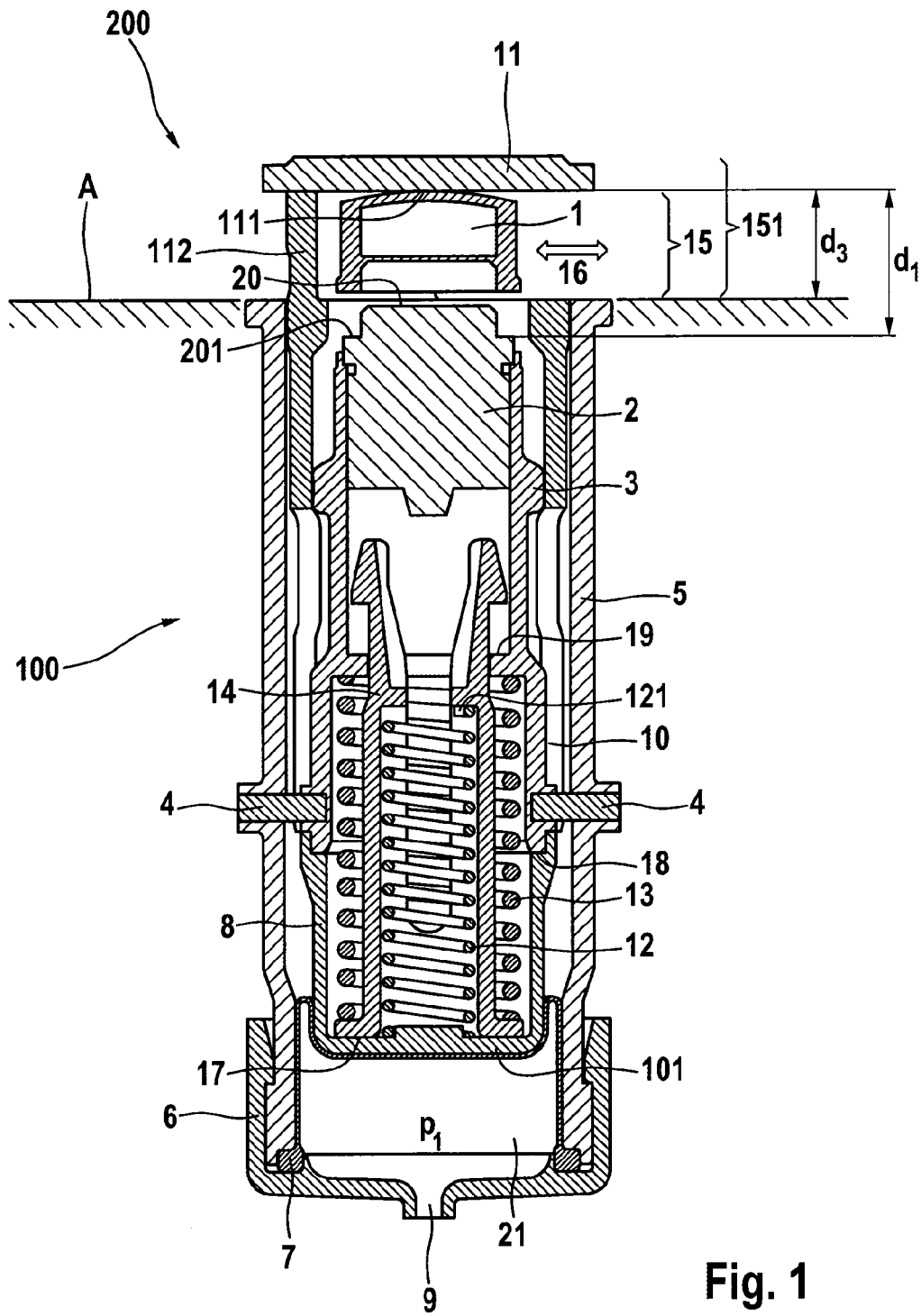
FIG. 1 schematically shows a longitudinal sectional view of a set-up position of a first embodiment of the device of the invention.

In the following, a possible embodiment of the method of the invention will be described. Reference will be made to the four positions shown in FIGS. 1 to 4 of an exemplary first realization or embodiment of the connection device of the invention and its constructive configuration, as well as the appended list of reference numerals.

FIG. 1 shows a connection device 100 of the invention in the so-called set-up position. The set-up position is suited for "setting up" an arrangement including at least one external functional device 1, i.e., for insertion of the external functional device 1 into a reception device 151, in particular into an opening or a gap or installation gap thereof.

In simpler terms, the connection device 100 of FIGS. 1 to 4 is constructed of three substantially cylindrical, coaxially nested hollow bodies having different diameters. A transition from the set-up position into another position may be effected by a pressing device and may be limited by defined stops.

The connection device 100 comprises a movable device such as, for example, a device imparting forces and/or movements and/or velocities. Among these are movable carrier members such as a central carrier 10, an opening actor subassembly 6, 7, 8 and 9 (in the following in short: 6-9) for applying a force, and energy storage and/or force transmitting devices having the form of a displacement spring 12 and a pressing spring 13.

The pneumatic opening actor subassembly 6-9 comprises a roller bellows 7, a pressurized air port 9, a piston 8, and a cylinder 6.

The opening actor subassembly 6-9 may alternatively also consist of, or comprise, a known piston/cylinder assembly (preferably including a piston sealing ring) or a linear drive (such as including an electrical drive mechanism).

The opening actor subassembly 6-9 may be configured to solely have a drive effect in the opening direction of the connection device 100.

The displacement spring 12 and the pressing spring 13 may in functional terms be included in a pressing device whereby the external functional device 1 may be pressed. The pressing device may comprise further elements.

The opening actor subassembly 6-9 may be configured for only being movable in a passive and/or braked manner in the closing direction of the pressing device.

For the purpose of pressing, at least one force is transmitted or applied by means of the opening actor subassembly 6-9 and/or energy storage and/or force transmitting devices to the movable carrier member 10 having a bottom 101.

FIG. 1 shows three nested hollow bodies. The outermost one of the three hollow bodies is referred to as an outer carrier 5. On its end face it may have a rigid, i.e. fixedly integrated, flange connection to the inside of an arrangement 200, for example a blood treatment apparatus, at the height of a coupling surface A for coupling an external functional device 1. The coupling surface A is a portion on the upper side of an outer carrier 5. It may, however, also be an outer sensor surface or a projection 201 of a sensor 2 fixedly integrated with the inner carrier 3, or any other portion appropriate for receiving a force.

Inside the outer carrier 5, the substantially cylindrical inner carrier 3 is held coaxially with the outer carrier 5 by means of rigid radial connection carriers 4. The sensor 2 carried by the inner carrier 3 is always arranged rigidly in a same position relative to the coupling surface A. Between the outer carrier 5 and the inner carrier 3 a free, regular, ring- or pipe-shaped gap is provided. The free end of the outer carrier 5 represented at the bottom side in the figures is closed by a bottom and comprises a pressure port 9.

As additional, nested hollow bodies a central carrier 10 and a spring dowel 14 are provided. These two hollow bodies are each and separately from each other displaceable in an axial direction inside the outer carrier 5.

The central carrier 10 is in the position of maximum extension, limited by the opening stop 18 which prevents further extension. The pressing spring 13 is tensioned and holds the spring dowel 14 pressed fixedly against the bottom 101 of the central carrier 10 at the lower dowel stop 17. As the pressing spring 13 has a higher force than the displacement spring 12, the displacement spring 12 is compressed to a defined length, namely, to the length of the interior space inside the spring dowel 14. The displacement spring 12 acts against the pressing spring 13. Altogether a resulting force $F_{2,\ set\text{-}up}$ acts as a pressing force.

The central carrier 10 is fixedly connected to a presser plate 11 on one of its end sides. The presser plate 11 is spaced apart from the coupling surface A at a variable spacing. In FIG. 1 the spacing is $d_3$. Two contact portions 111 and 201 are arranged at a first spacing $d_1$ from each other. In the embodiment shown in the figures, the coupling surface A might also act as a contact portion. Nevertheless, in the following the corresponding surface of the presser plate 11 shall mainly be mentioned as the further contact portion 111.

The movable central carrier 10 has recesses at its circumference through which connection carriers 4 project into the interior of the central carrier 10. The central carrier 10 is adapted for a limited axial displacement in the annular gap between the outer carrier 5 and the inner carrier 3.

Inside the central carrier 10 the spring dowel 14 is arranged. The spring dowel 14 is adapted for an axial displacement relative to an interior of the inner carrier 3. The central carrier 10 is closed on its other end side (represented in FIG. 1 as the lower end side) by its bottom 101.

The presser plate 11, a portion 112 of the central carrier 10 and the upper side of the sensor 2, or a portion 201 of the sensor 2, are part of the reception device 151 presently having a C-shaped configuration.

In the range of the bottom of the outer carrier 5 the opening actor subassembly 6-9 is arranged.

The opening actor subassembly 6-9 comprises an air-tight roller bellows 7. The latter may be arranged in a peripherally sealing manner such that a pneumatic work space 21 is created between the bottom 101 and the roller bellows 7. The roller bellows 7 rests externally on the bottom 101 of the central carrier 10 from below. It seals the work space 21 against the ring gap between the central carrier 10 and the outer carrier 5.

In order to receive an external functional device 1, air, some other gas or some other fluid under a first pressure $p_1$ is pressed into the work space 21 via the pressurized air port 9. The roller bellows 7 presses against the bottom 101 of the central carrier 10 and displaces the central carrier 10—as a function of the first pressure $p_1$—axially out of the outer carrier 5.

The presser plate 11 rises and moves away from the coupling surface A. The presser plate 11 and the coupling surface A are then spaced apart at a spacing $d_3$ as mentioned in the foregoing, which may be seen in FIG. 1. The spacing $d_3$ forms an opening or a gap, or installation gap 15, for receiving an external functional device 1.

The external functional device 1 may be inserted into the installation gap 15 by a horizontally performed movement 16 marked by an arrow in FIG. 1. In this position, the spacing $d_1$ for the external functional device as mentioned in the foregoing results between the contact portions 111 and 201.

The spring dowel 14 may be mounted or supported by the two springs 12 and 13 against the central carrier 10 and the inner carrier 3. The stronger and larger spring 13 having a spring force $FE_1$ is referred to as a pressing spring 13 in accordance with its function, and the weaker and smaller spring 12 having a spring force $FE_2$ is referred to as a displacement spring 12 in accordance with its function.

Due to the convoluted force relations resulting, for example, from elastic deformations of the structural components and stops involved, direction of the force effect of the springs etc., the practical examples generally do not represent the clear-cut spring forces $FE_1$ and $FE_2$ of displacement spring 12 and pressing spring 13. The springs 12 and 13 may generally be subjected to a bias in any position of the connection device. The extent of their respective biases may vary as a function of the respective position of the connection device.

The displacement spring 12 is mounted inside the spring dowel 14 with one of its ends against a stop 121 and presses with its other end against the inner side of the bottom 101 of the central carrier 10. The end of the spring dowel 14 facing the bottom 101 of the central carrier 10 comprises an external flange.

The other end of the spring dowel 14 is realized or provided as a flexible snap-action device. During assembly of the connection device 100 of the invention it may be locked at the arrangement 200 in the opening of an upper dowel stop 19 of the inner carrier 3.

On the one hand, as a result of installing the displacement spring 12, owing to the tolerances between the outer diameter of the displacement spring 12 and the inner diameter of the spring dowel 14 in the range of the displacement spring 12 ("residual gap"), the snap-action device is secured against compression whereby the spring dowel 14 is locked inside the inner carrier 3. Hereby, it is ensured that an inadvertent release of the snap-type connection due to compression of the spring dowel 14 or a lasting bending deformation of the spring dowel 14 does not come about during operation.

On the other hand, the residual gap is realized or provided in an appropriate manner both for installation and disassembly, so that friction between the outer diameter of the displacement spring 12 and the inner diameter of the spring dowel 14 is prevented across the length of the displacement spring 12.

It is basically sufficient if the displacement spring 12 secures the spring dowel 14 against radial compression only by its annular end due to form closure connection. To this end, the receiving support surface of the upper end of the displacement spring 12 may be realized in the spring dowel 14 as a short stepped shoulder into which the end of the spring is fitted such that the residual gap may otherwise be provided with a relatively large width.

It is, however, also possible to make the inner part of the spring dowel 14 conical substantially across its entire or substantially entire length or across a portion thereof, so that the displacement spring 12 may be installed and disassembled easily, but inadvertent releasing of the snap-type connection is nevertheless prevented. The upper end of the displacement spring 12 is then mounted in the conical, narrowly tapering part of the cone inside the spring dowel 14 and prevents a compression of the spring dowel 14.

The pressing spring 13 surrounds portions of the spring dowel 14. One end is pressed against the external flange of the spring dowel 14, and the other end is pressed against the upper dowel stop 19 of the inner carrier 3.

The displacement spring 12 and the pressing spring 13 may be compressed with the aid of the opening actor subassembly 6-9.

The set-up position shown in FIG. 1 is obtained with the aid of the opening actor subassembly 6-9. During the transition from the set-up position shown in FIG. 1, the opening actor subassembly 6-9 overcomes the forces of springs 12, 13 acting against it and the frictional forces between structural components 2, 3, 4 and 5 being at rest and movable structural components 7, 8, 10, 11, 12, 13 and 14 of the connection device 100 of the invention. In the set-up position the two springs 12, 13 are compressed in a maximum degree.

When the central carrier 10 abuts against an opening stop 18 of the inner carrier 3, the opening movement of the installation gap 15 is terminated. The spring dowel 14 is raised up from the upper dowel stop 19 of the inner carrier 3 to a maximum extent.

During manual insertion (or also removal) of the external functional device 1 from the installation gap 15, the opening actor subassembly 6-9 continues to be switched to the active state.

The opening or the installation gap 15 of the reception device 151 may, however,—in difference from the representation in the figures—also take place without an effect or presence of the opening actor subassembly 6-9. To this end, the user of the arrangement 200 may use his fingers, for instance. He may manually pull up the reception device 151. For better handling or better engagement with the finger(s), a grasping device such as a handle, a lug, a ring or the like may be provided. This grasping device (not shown) may be fastened to the outer surface of the presser plate 11. This embodiment represents a particularly low-cost embodiment of the present invention. Furthermore, it advantageously allows operation, setting up, or dismantling of the arrangement 200 even in the case of a power failure. It may thus supplementarily also be provided for allowing an emergency operation.

In the set-up position, the installation gap 15 is large enough to allow an ergonomically favorable insertion and removal of the external functional device 1. Due to the size of the installation gap 15, however, inadvertent introduction of an operator's fingers, for instance, is also possible.

FIG. 1 moreover shows a lower dowel stop 17 and a coupling stop 20.

Figure 2:
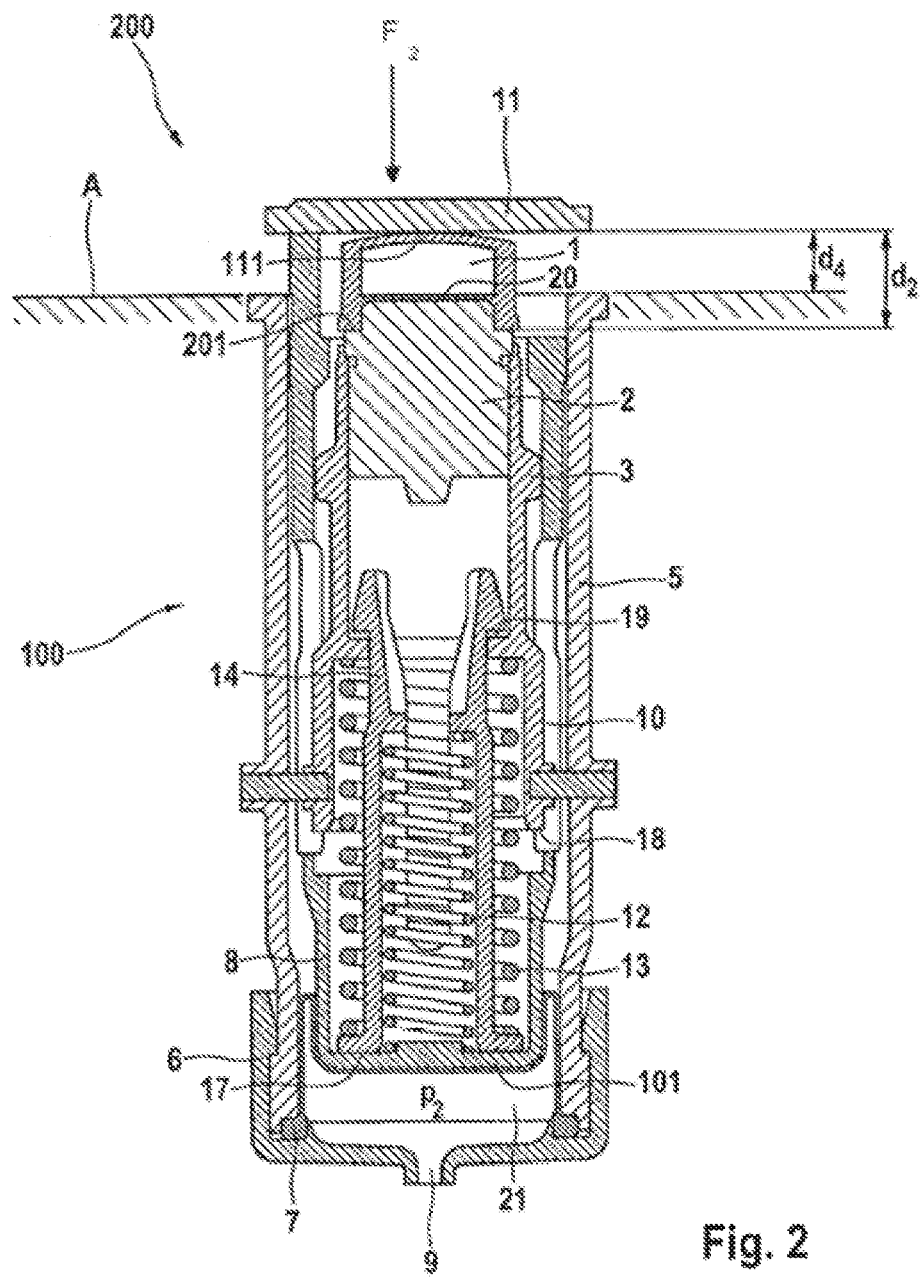
FIG. 2 schematically shows a longitudinal sectional view of a work position of the embodiment of FIG. 1.

In order to press the external functional device 1 with the arrangement and couple it to the latter, the device of the invention is displaced into the work position, as is shown in FIG. 2.

In the work position, the presser plate 11 and the coupling surface A are spaced apart at a spacing $d_4$, as is visible in FIG. 2. Between the first contact portion 111 and the further contact portion 201 for receiving the external functional device 1 the second spacing $d_2$ results in this position.

The work position of the connection device 100 of the invention is driven at or reached after switching the opening actor subassembly 6-9 to the passive state. The work position may be reached by releasing the tension applied by the finger in the embodiment that was discussed as an alternative for FIG. 1.

The two springs 12 and 13 drive the movable structural components 7, 8 of the connection device 100 of the invention against existing frictional resistances.

Inside the work space 21, a pneumatic second pressure $p_2$ is applied. The second pressure $p_2$ is lower than the first pressure $p_1$ prevailing in the set-up position of FIG. 1. The central carrier 10 is urged into the work space 21 until the sum of the spring forces $FE_1$ and $FE_2$ has been received by the external functional device 1 and the work position at the coupling stop 20 on a portion of the upper side of the outer carrier 5, or on a surface of the sensor 2, has been reached.

In comparison with the set-up position of FIG. 1, the central carrier 10 is in a less extended position. The pressing spring 13 is compressed less than in the set-up position (FIG. 1). The central carrier 10 is raised from the opening stop 18 of the inner carrier 3. Like in the set-up position, the spring dowel 14 is fixedly pressed against the bottom 101 of the central carrier 10 by the pressing spring 13 on the lower dowel stop 17. Like in the set-up position (FIG. 1), the displacement spring 12 is compressed to the length of the interior space inside the spring dowel 14. The spring dowel 14 does not contact the upper dowel stop 19. The displacement spring 12 acts against the pressing spring 13. Altogether, a resulting force $F_2$ acts as a pressing force. In the work position, the force $F_{2,\,work}$ is only slightly lower than in the set-up position (FIG. 1) owing to the flat characteristic line (force/path diagram, see FIG. 6).

The spring dowel 14 remains at the lower dowel stop 17 until the work position and coupling at the coupling stop 20 are reached.

Force transmission takes place in such a way that the coupling force between the external functional device 1 and a coupling partner 2 such as, for example, a sensor, rises on the side of the arrangement, or on the second contact portion 201, from zero to a value somewhat below the biasing force of the pressing spring 13, while the force acting on the opening actor subassembly 6-9 drops to the differential value that depends on friction and residual bias.

In order to guarantee secure pressing even under consideration of possible tolerances and resiliency of the components of the external functional device 1 and of the components of the device of the invention or of the arrangement, a provided reserve path remains in the direction of pressing, which is visible by the spacing of the two stop partners of the upper dowel stop 19 in FIG. 2.

Following utilization of the external functional device in the work position, for example following completion of a medical treatment, the opening actor subassembly 6-9 displaces the movable structural components 11, 12, 13 and 14 of the connection device 100 of the invention back into the set-up position under the opposed force at least of the pressing spring 13 and of the frictional forces. The external functional device 1 may be removed from the installation gap 15.

The displacement spring 12 which is biased and designed to be weaker permanently remains at its approximately constant bias value during the set-up/work cycle of the connection device 100 of the invention.

The lower dowel stop 17 does not disengage or does not become released or spaced apart from the bottom 101. The displacement spring 12 remains enclosed, due to form closure and frictional connection, in a constant position in its installation space.

In prior-art devices, the operating personnel may get injured above all during the transition from the set-up position into a closure position or during the transition from the set-up position into the work position while the external functional device 1 is not inserted in the installation gap 15.

The path from the set-up position into a closure position is subdivided into two phases of movement in the framework of the present description. The first one characterizes the transition from the set-up position into a force change position. The second one characterizes the transition from the force change position into the closure position.

Figure 3:
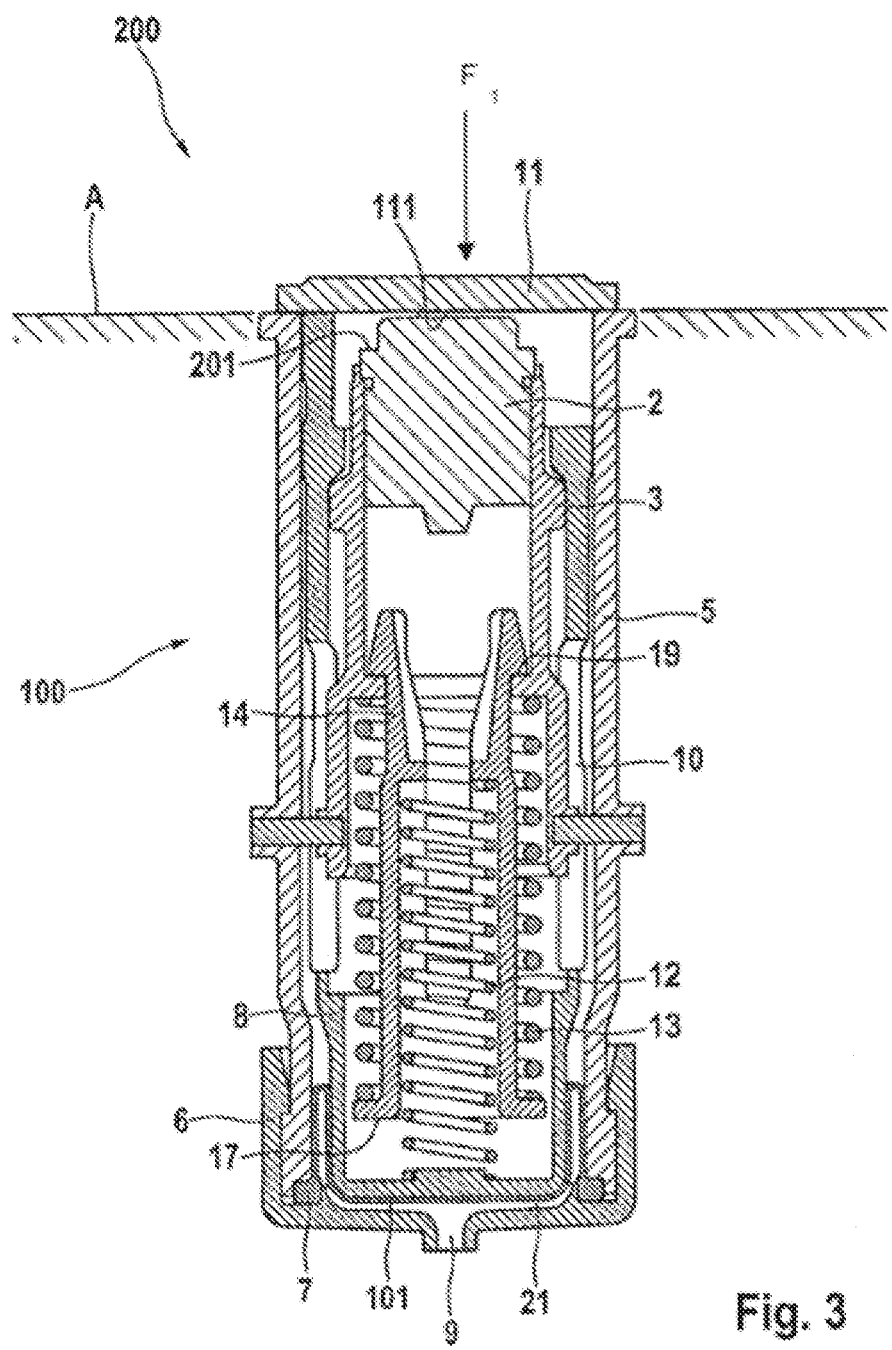
FIG. 3 schematically shows a longitudinal sectional view of a closure position of the embodiment of FIG. 1.

FIG. 3 shows a connection device 100 of the invention in the so-called closure position.

The two springs 12, 13 each present a maximum possible excursion. Inside the work space 21 the pneumatic overpressure is as low as possible while preferably tending towards zero. Thus a large proportion of the remaining bias of the displacement spring 12 may be utilized as a sealing force between the presser plate 11 and the outer carrier 5. This may advantageously be used for achieving the lowest possible specified force, which in turn allows a simplified, less bulky and less costly construction.

During the transition into the closure position, the central carrier 10 is urged into the work space 21 by the displacement spring 12. The work space 21 has a minimum volume.

In the closure position, the central carrier 10 is in a completely retracted position. The lower dowel stop 17 is raised from the bottom 101 of the central carrier 10. The pressing spring 13 extends to such a degree that the upper dowel stop 19 is pressed against the stationary inner carrier 3. As soon as the upper dowel stop 19 is pressed against the stationary inner carrier 3 and the central carrier 10 is retracted further, the displacement spring 12 extends out of the interior space of the spring dowel 14. In the closure position, the force of the pressing spring 13 is received entirely by the spring dowel 14 and results in corresponding elastic deformations of the spring dowel 14. The pressing spring 13 does in this position not act directly on the central carrier 10. Only the displacement spring 12 acts directly on the bottom 101 of the central carrier 10. The resulting lower force $F_{1,\ closure}$ acts between presser plate 11 and coupling surface A.

Between the inner side of the bottom 101 of the central carrier 10 and the external flange of the spring dowel 14 there is a guaranteed free space, so that the work fluid may exert its pressure on the entire piston surface during the opening stroke. The spring dowel 14 rests against the upper dowel stop 19 of the inner carrier 3.

The presser plate 11 substantially contacts the coupling surface A, in the present instance a portion of the upper side of the outer carrier 5.

The present position of FIG. 3 is referred to as the closure position, for the presser plate 11 closes access to the sensor 2 or to an interior of the connection device 100 of the invention or of the arrangement 200 against the environment. Hereby, a sealing of the connection device 100 of the invention against an outside of the arrangement 200 may be achieved.

Figure 4:
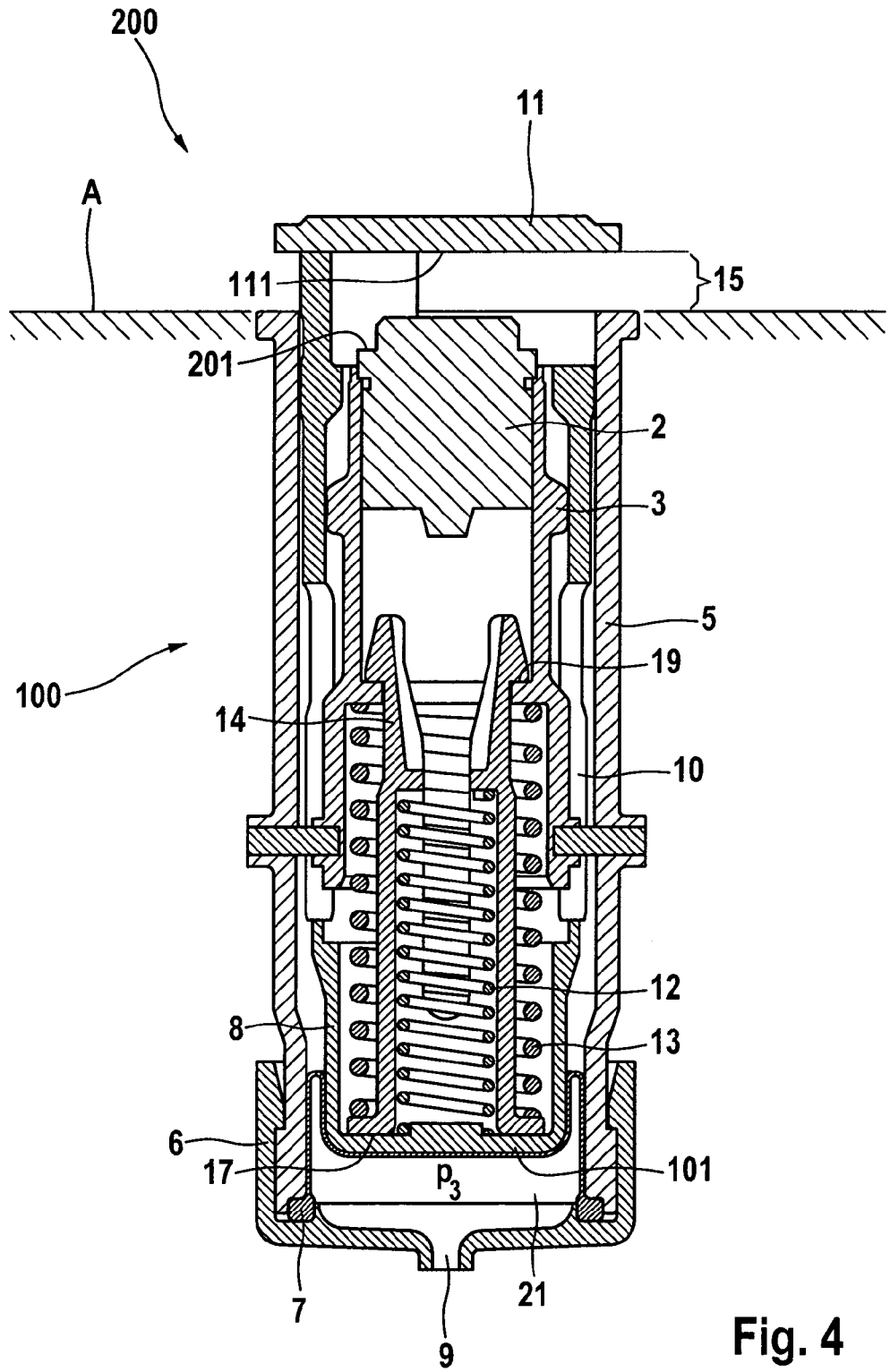
FIG. 4 schematically shows a longitudinal sectional view of a force change position of the embodiment of FIG. 1.

During the displacement or transition into the closure position, the connection device 100 of the invention passes through a force change position, as is shown in FIG. 4. In the force change position of FIG. 4, the third pressure $p_3$ in the pneumatic work space 21 is higher than zero. For the pressure, pressures in the overpressure range relative to the environmental pressure are generally applied.

The pneumatic force acting on the bottom 101 of the central carrier 10 exceeds the spring force $FE_2$ of the displacement spring 12. The displacement spring 12 is compressed to the maximum.

The external flange of the spring dowel 14 rests against the lower dowel stop 17 at the bottom of the central carrier 10. The third pressure $p_3$ is high enough for the pressing spring 13 to maintain a length and bias predetermined by contact of the spring dowel 14 against the upper dowel stop 19. For a further displacement of the central carrier 10 from the force change position in a direction towards the closure position, the pneumatic pressure $p_3$ has to be lowered to such an extent to allow a further extension of the biased displacement spring 12.

Initially a force $F_2$ prevails, which drops abruptly upon further displacement of the connection device into the work position and is reduced to a very much lower force $F_1$. This evolution is illustrated by way of example in the appended force/path diagram of FIG. 6, when viewed from the right to the left.

The force change position is a transitional position that is passed through upon changing from the set-up position to the closure position, and vice versa. When the change takes place from the closure position towards the set-up position, i.e., the central carrier 10 is extended starting at the closure position (FIG. 3), the displacement spring 12 is compressed increasingly, and an operating point is reached at which the upper dowel stop 19 continues to rest against the inner carrier 3 and the lower dowel stop 17 gets into contact with the bottom 101 of the central carrier 10. This operating point is represented in the force/path diagram by a first discontinuity 41. The force of the pressing spring 13 is in this operating point still received entirely between spring dowel 14 and inner carrier 3 and does not yet act directly on the central carrier 10. Only the force of the displacement spring 12 acts directly on the central carrier 10. A resulting low force $F_{1,\ force\ change}$ acts on a potential object (e.g. finger) between presser plate 11 and coupling surface A. This force is not capable of injuring body parts such as fingers possibly present between presser plate 11 and coupling surface A.

Upon further extension of the central carrier 10 beyond the described operating point, the elastic component behavior of all of the structural components, e.g. of the spring dowel 14, of the central carrier 10 and of the inner carrier 3, of the outer carrier 5 together with the springs 12 and 13 taken together results in a short range of a steep increase in the force/path diagram concurrently with an increasing extension of the central carrier 10. In this range, force is increasingly transmitted to the bottom 101 of the central carrier 10, and the spring dowel 14 rising from the inner carrier 3 at the upper dowel stop 19 is increasingly relieved. The transition in the range of forces $F_2$ is represented in the force/path diagram as a second discontinuity 43.

If during the first phase of movement of the transition from the set-up position into the closure position or of the transition from the set-up position into the work position a sufficiently large object is introduced into the installation gap 15, the closing movement comes to a stop at this object. The installation gap 15 is, however selected to be so large in this first phase of movement that inadvertently introduced fingers may not yet be pinched painfully.

The effect of force on the introduced object or finger due to the biasing force of the pressing spring 13, in a given case reduced by the frictional resistances of the device 100 of the invention, can not seriously injure a finger owing to the remaining gap width.

The force change position according to FIG. 4, when observing a transition from the set-up position in a direction towards the closure position, is removed towards the work position by the above-mentioned reserve path and presents a correspondingly reduced installation gap 15. In the force change position, the upper dowel stop 19 enters into engagement or the spring dowel 14 rests on it, respectively. This is accompanied by an increase of the force on this upper dowel stop 19, from zero to the bias value of the pressing spring 13.

The pressing spring 13 now only acts within a mechanically closed space of spring dowel 14 and inner carrier 3.

During the second phase of movement—from the force change position into the closure position—the displacement spring 12 having a weaker bias may now become active. Its force $FE_2$ acts to overcome the frictional resistances of the connection device 100 of the invention and in particular of the opening actor subassembly 6-9 to achieve the further closing movement to the closure position, as is represented in FIG. 3.

The biasing force of the displacement spring 12 is selected such that in combination with the conformation and/or size of the installation gap 15 existing during this phase of movement it is not capable of causing any painful injuries to fingers, such as bruises.

On the other hand, the selected biasing force of the displacement spring 12 is high enough to achieve—due to the sealing force acting in the closure position between the sealing rim of the presser plate 11 and the sealing rim of the outer carrier 5 in combination with suitable sealing elastomers—a sufficient tightness of the closed arrangement against the entrance of particles and liquids.

In the following a second embodiment of the method of the invention shall be described by making reference to the four key positions of the connection device of the invention as described in FIGS. 1 to 4.

The second embodiment corresponds in its configuration to the above-described embodiment. Concerning the second embodiment, exemplary dimensions for the configuration of the connection device 100 of the invention or of portions thereof shall be given in the following.

In a set-up position of the connection device 100 of the invention, an installation gap 15 may have a dimension of, e.g., 18 or 19 mm (millimeters). Due to the stops, the pressing spring 13 has a minimum length of 57 mm. The displacement spring 12 may have a length of 55 mm. The distance between the bottom 101 of the central carrier 10 and the inlet of the pressure port 9 may be 26 mm. The volume of the work space 21 becomes a maximum value.

In the work position of the connection device 100 of the invention, the height of the installation gap 15 substantially corresponds to the height of the external functional device 1—which, in a given case, is pressed only little or, however, more strongly—and is, e.g. 11, 12 or 13 mm. The pressing spring 13 may have a length of 64 mm; the displacement spring 12 may have a length of 54 mm. The distance between the bottom 101 of the central carrier 10 and the inlet of the pressure port 9 may be 18 mm.

In the closure position the presser plate 11 rests on the outer carrier 5. The height of the installation gap 15 accordingly is substantially zero. The pressing spring 13 is biased and may have a length of 66 mm. This may correspond to its maximum possible length due to the stops. The displacement spring 12 may have a length of 65 mm. The distance between the bottom of the central carrier 10 and the inlet of the pressure port 9 may be 7 mm. The volume of the work space 21 becomes a minimum value. A free space formed between the outer side of the bottom of the spring dowel 14 and the inner side of the bottom 101 of the central carrier 10 may have a height of 10 mm.

In the force change position, the height of the installation gap 15 may be 10, 11 or 12 mm, for example. Due to the stops, the pressing spring 13 may have a maximum possible length of 66 mm. The displacement spring 12 may have a length of 56 mm. The distance between the bottom 101 of the central carrier 10 and the inlet of the pressure port 9 may be 17 mm.

All of the dimensions given in the present application, in particular those indicated in millimeters, represent exemplary values. The present invention is not restricted to them. It is moreover noted that the dimensions may, of course, be adapted to national and regional safety regulations and to wishes of users or purchasers of the present invention.

Figure 5:
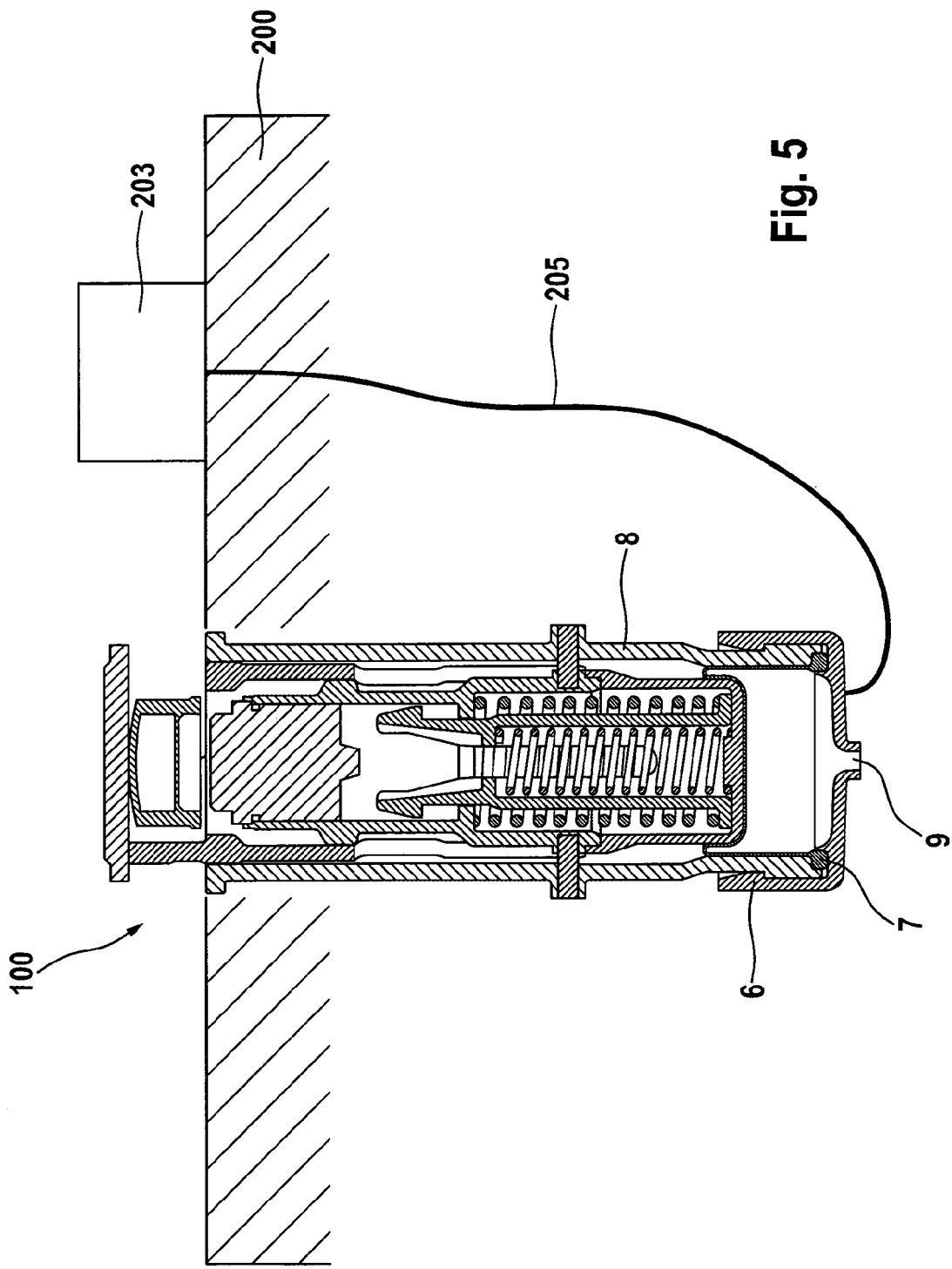
FIG. 5 shows an arrangement of the invention in a simplified representation as a partial block diagram.

FIG. 5 is a simplified representation of a blood treatment arrangement as an example of an arrangement 200 of the invention as a partial block diagram. The arrangement 200 comprises a connection device 100 having an opening actor subassembly 6-9. It further comprises a control device 203 for acting on the opening actor subassembly 6-9. A control line 205 is provided between the opening actor subassembly 6-9 and the control device 203.

To the person having skill in the art it is evident that the embodiment shown in FIG. 5 may be realized with any connection device in accordance with the invention and not only with the one shown there. The representation of the connection device 100 in FIG. 5 in its specific configuration merely serves for enhanced comprehension.

FIG. 6 shows an example of a force/path diagram.

On the x-axis, various positions of the connection device of the invention are represented as were described in detail by making reference to FIGS. 1 to 4: a closure position 23, a force change position 25, a work position 27, and a set-up position 29.

The numeric indications in [mm] indicate the respective associated displacement of the contact portions or the gap width d, respectively.

For example, a mutual spacing of the contact portions is 0 mm in the closure position 23, 12 mm in the force change position 25, 13 mm in the work position 27, and 18 mm in the set-up position 29.

On the y-axis, the force F is indicated in [N]. The bold, solid line 30a represents the force evolution of the force acting on the external functional device, on a finger, on a sealing partner, etc. It indicates a statistical state.

The dashed line 30b and the dash-dotted line 30c represent force evolutions of the opening actor or of the opening actor subassembly, respectively. The dashed line 30b represents the resulting force of the opening actor during opening. The dash-dotted line 30c represents the resulting force of the opening actor upon closing.

The force evolution generally usual during a utilization of the connection device is shown in FIG. 6 from right to left.

The connection device initially is present in the set-up position 29. In the set-up position 29, the connection device may receive an external functional device.

During displacement of the connection device from the set-up position 29 into the closure position 23 for functional coupling of the external functional device, initially an absolute second force $F_2$ of about 130 N is applied to the connection device. Upon further displacement, the force $F_2$ drops during a first force range 31 having a first gradient 33 all the way to the work position 27.

From the work position 27, the force acting on the connection device further drops all the way to the force change position 25. In the range of the force change position 25, a total deformation of about 0.2 mm occurs, as is shown in FIG. 6.

In the portion 35 of total deformation, the force drops abruptly from the first force range 31 from a second force $F_2$ of about 125 N to a second force range 37 to a force $F_1$ of about 25 N. Accordingly, a first discontinuity 41 occurs upon transition from the first force range 31 into the portion 35 of total deformation. Upon transition across the portion 35 of total deformation in the second force range 37, a second discontinuity 43 occurs.

In the range of the force change position 25 and of the closure position 23, a force $F_1$ within the second force range 37 substantially acts.

During displacement of the connection device from the force change position 25 into the closure position 23, the force $F_1$ drops at a second gradient 39.

An absolute force $F_1$ in the closure position 23 may be, e.g., about 20 N.

As may be taken from the force/path diagram, the external functional device only receives either the force $F_1$ or the force $F_2$.

The present invention is not restricted to the embodiments presently described; these merely serve for illustration.

What is claimed is:

1. A connection device for connecting at least one medical external functional device to an arrangement by pressing the medical external functional device, the connection device comprising at least an outer carrier, an inner carrier inside the outer carrier, and a central carrier therebetween, said connection device further comprising:
    at least one reception device comprising at least one first contact portion on the central carrier configured to receive the medical external functional device between the first contact portion and at least one further contact portion on the inner carrier, wherein the first contact portion is arranged at a variable spacing (d) from the further contact portion; and
    at least one pressing device comprising a first spring arranged inside of the inner carrier, and a second spring coaxial with the first spring, the first and second springs configured to reduce the variable spacing (d) in order to press the medical external functional device between the first contact portion and the further contact portion by transferring at least the first contact portion from a first position, in which a first spacing (d1) between the first contact portion and the further contact portion is present, into a second position, in which a second spacing (d2) between the first contact portion and the further contact portion is present, wherein said second spacing (d2) is smaller than the first spacing (d1);
    wherein the pressing device is configured to transfer at least the first contact portion from the first position into the second position by applying a first force (F1) via the first spring and a second force (F2) via the second spring, said first force (F1) and said second force (F2) being of a different magnitude.

2. The connection device according to claim 1, wherein the magnitude of the first force ($F_1$), the second force ($F_2$), or both are dependent on the spacing ($d_1$).

3. The connection device according to claim 1, wherein the first spring and the second spring are configured such that the first spring exerts the first force (F1) during the transition from the first position to a force change position, and the second spring exerts the second force (F2) during the transition from the force change position to the second position.

4. The connection device according to claim 1, wherein the first spring and the second spring are configured such that the first spring together with the second spring exerts the first force (F1) during the transition from the first position to a force change position, and the second spring exerts the second force (F2) during the transition from the force change position to the second position.

5. The connection device according to claim 1, wherein the second force ($F_2$) is higher than the first force ($F_1$).

6. The connection device according to claim 1, wherein the second position is a work position in which the medical external functional device is adapted to be pressed with the arrangement.

7. The connection device according to claim 1, wherein the second position is a closure position in which the first contact portion effects sealing.

8. The connection device according to claim 1, further comprising:
    a pneumatically acting or pneumatically operable opening actor subassembly configured to compress the first spring and the second spring to transfer at least the first contact portion from the second position into the first position.

9. The connection device according to claim 1, wherein the first position is a set-up position in which the at least one reception device has an opening sufficiently large to receive the medical external functional device.

10. A blood treatment apparatus comprising:
    at least one connection device configured to connect at least one external functional device to the blood treatment apparatus by pressing the external functional device, the connection device comprising at least an outer carrier, an inner carrier inside the outer carrier, and a central carrier therebetween, said connection device further comprising:
    at least one reception device comprising at least one first contact portion on the central carrier configured to receive the external functional device between the first contact portion and at least one further contact portion on the inner carrier, wherein the first contact portion is arranged at a variable spacing (d) from the further contact portion; and
    at least one pressing device comprising a first spring arranged inside of the inner carrier, and a second spring coaxial with the first spring, the first and second springs configured to reduce the variable spacing (d) in order to press the external functional device between the first contact portion and the further contact portion by transferring at least the first contact portion from a first position, in which a first spacing between the first contact portion and the further contact portion is present, into a second position, in which a second spacing between the first contact portion and the further contact portion is present, wherein said second spacing is smaller than the first spacing;
    wherein the pressing device is configured to transfer at least the first contact portion from the first position into the second position by applying a first force (F1) via the first spring and a second force (F2) via the second spring, said first force (F1) and said second force (F2) being of a different magnitude.

11. The blood treatment apparatus according to claim 10, further comprising:

a control or regulation device configured to control or regulate a pneumatically acting or pneumatically operable opening actor subassembly of the connection device.

12. The blood treatment apparatus according to claim 10, further comprising: an external functional device.

13. The blood treatment apparatus according to claim 12, wherein the external functional device is adapted to be coupled by frictional connection, a form closure connection, or both to the blood treatment apparatus, in order to functionally couple the external functional device to a coupling partner on the side of the blood treatment apparatus.

* * * * *